United States Patent
Schaefer et al.

(10) Patent No.: US 8,787,646 B2
(45) Date of Patent: Jul. 22, 2014

(54) METHOD AND APPARATUS FOR COMPUTED TOMOGRAPHY IMAGE RECONSTRUCTION

(75) Inventors: Dirk Schaefer, Hamburg (DE); Michael Grass, Bucholz in der Nordheide (DE)

(73) Assignee: Koninklijke Philips N.V., Eindhoven (NL)

( * ) Notice: Subject to any disclaimer, the term of this patent is extended or adjusted under 35 U.S.C. 154(b) by 458 days.

(21) Appl. No.: 13/254,001

(22) PCT Filed: Feb. 18, 2010

(86) PCT No.: PCT/IB2010/050721
§ 371 (c)(1),
(2), (4) Date: Aug. 31, 2011

(87) PCT Pub. No.: WO2010/109352
PCT Pub. Date: Sep. 30, 2010

(65) Prior Publication Data
US 2012/0014582 A1    Jan. 19, 2012

Related U.S. Application Data

(60) Provisional application No. 61/163,489, filed on Mar. 26, 2009.

(51) Int. Cl.
*G06K 9/00*    (2006.01)
*G06T 11/00*    (2006.01)
*A61B 6/03*    (2006.01)
*A61B 6/02*    (2006.01)

(52) U.S. Cl.
CPC ............. *G06T 11/005* (2013.01); *A61B 6/027* (2013.01); *A61B 6/032* (2013.01)
USPC ........................................................ 382/131

(58) Field of Classification Search
None
See application file for complete search history.

(56) References Cited

U.S. PATENT DOCUMENTS

| | | | | |
|---|---|---|---|---|
| 5,848,117 A | * | 12/1998 | Urchuk et al. | 378/19 |
| 5,987,091 A | | 11/1999 | Miyazaki et al. | |
| 7,424,088 B2 | * | 9/2008 | Zamyatin et al. | 378/4 |
| 2006/0067457 A1 | * | 3/2006 | Zamyatin et al. | 378/4 |

(Continued)

FOREIGN PATENT DOCUMENTS

| | | |
|---|---|---|
| EP | 0124015 A2 | 11/1984 |
| EP | 0430550 A2 | 6/1991 |
| WO | 9823209 A1 | 6/1998 |
| WO | WO 2010/070527 A2 * | 6/2010 |

OTHER PUBLICATIONS

Cho, Paul S. et al., "Cone-beam CT for radiotherapy applications," Phys. Med. Biol. 40 (1995) pp. 1863-1883.

(Continued)

*Primary Examiner* — Tahmina Ansari (57) ABSTRACT

A method and apparatus are provided to reconstruct projection data obtained from CT imaging devices with offset detector geometries. According to one aspect of the present invention, a method is provided to reconstruct projection data obtained from CT imaging devices with offset detector geometries that includes the following steps: (i) matching projection data measured at opposing sides of the acquisition trajectory and splicing them together to generate a full, non-truncated projection data set; (ii) differentiation of the projection data; (iii) filtering the differentiated projection data with a filter, such as for example a Hilbert filter; (iv) applying redundancy weighting to the filtered projection data; and (v) back-projecting the redundancy weighted projection data to generate image data.

23 Claims, 6 Drawing Sheets

(56) References Cited

U.S. PATENT DOCUMENTS

| | | | |
|---|---|---|---|
| 2007/0121779 A1* | 5/2007 | Nishide et al. | 378/4 |
| 2011/0085637 A1* | 4/2011 | Boese et al. | 378/4 |
| 2011/0255657 A1* | 10/2011 | Noordhoek | 378/11 |
| 2012/0014582 A1* | 1/2012 | Schaefer et al. | 382/131 |
| 2013/0077847 A1* | 3/2013 | Hansis et al. | 382/131 |

OTHER PUBLICATIONS

Cho, Paul S. et al., "Cone-beam CT from width-truncated projections," Computerized Medical Imaging and Graphics, vol. 20, No. 1, pp. 49-57, 1996.

Clackdoyle, Rolf et al., "Quantitative reconstruction from truncated projections in classical tomography," IEEE Transactions on Nuclear Science, vol. 51, No. 5, Oct. 2004, pp. 2570-2578.

Crawford, C. R., et al.; Computed tomography scanning with simultaneous patient translation; 1990; Medical Physics; 17(6)967-982.

Feldkamp, L. A. et al, "Practical cone-beam algorithm," J. Opt. Soc. Am. A/vol. 1, No. 6/Jun. 1984, pp. 612-619.

Gomi, T. et al., "Development of a new three-dimensional image reconstruction algorithm to reduce cone-beam artifacts," Proceedings of the SPIE—The International Society for Optical Engineering vol. 5745, No. 1 : 1046-56, Apr. 2005.

Gullberg, Grant T. et al., "Reconstruction Algorithm for Fan Beam with a Displaced Center-of-Rotation," IEEE Transactions on Medical Imaging, vol. MI-5, No. 1, Mar. 1986; pp. 23-29.

Hsieh, J., "Investigation of 3D Image Artifact Caused by Projection Weighting and Misalignment," Image Processing, 1999. ICIP 99 Proceedings. 1999 International Conference. Meeting Date: Oct. 24, 1999-Oct. 28, 1999. vol. 2, pp. 681-685.

Katsevich, Alexander, "Analysis of an exact inversion algorithm for spiral cone-beam CT," Phys. Med. Biol. 47 (2002), pp. 2583-2597.

Leng, Shuai et al., "Exact fan-beam image reconstruction algorithm for truncated projection data acquired from an asymmetric half-size detector," Phys. Med. Biol. 50 (2005), pp. 1805-1820.

Li, Liang et al., "A new cone-beam X-ray CT system with a reduced size planar detector," High Energy Physics and Nuclear Physics, vol. 30, No. 8, Aug. 2006, pp. 812-817.

Liu, Vinson et al., "X-ray micro-CT with a displaced detector array: application to helical cone-beam reconstruction," Med. Phys. 30 (10), Oct. 2003, pp. 2758-2761.

Noo, Frederic et al., "A new scheme for view-dependent data differentiation in fan-beam and cone-beam computed tomography," Phys. Med. Biol. 52 (2007) pp. 5393-5414.

Noo, Frederic et al., "Image reconstruction from fan-beam projections on less than a short scan," Phys. Med. Biol. 47 (2002) pp. 2525-2546.

Parker, Dennis L., "Optimal short scan convolution reconstruction for fanbeam CT," Med. Phys. 9(2) Mar./Apr. 1982, pp. 254-257.

Wang, Ge, "X-ray micro-CT with a displaced detector array," Med. Phys. 29 (7), Jul. 2002, pp. 1634-1636.

Yu, Lifeng et al., "Applicaton of asymmetric cone-beam CT in radiotherapy," 0-7803-8701-5/04 2004 IEEE, 4 pages.

Yu, Hengyong et al., "Feldkamp-type VOI reconstruction from super-short-scan cone-beam data," Med. Phys. 31 (6), Jun. 2004, pp. 1357-1362.

Zamyatin, Alexander A. et al., "Helical cone beam CT with an asymmetrical detector," Med. Phys. 32 (10), Oct. 2005, pp. 3117-3127.

* cited by examiner

METHOD AND APPARATUS FOR COMPUTED TOMOGRAPHY IMAGE RECONSTRUCTION

CROSS REFERENCE TO RELATED APPLICATIONS

This application claims the benefit of U.S. provisional application Ser. No. 61/163,489 filed Mar. 26, 2009, which is incorporated herein by reference.

The present application relates generally to the medical imaging arts. More specifically, it provides a method and apparatus for the reconstruction of computed tomography (CT) images. The application subject matter finds use at least with x-ray CT imaging and will be described with particular reference thereto. However, it also has more general application with other imaging methods and in other arts, such as single-photon emission computed tomography (SPECT) or positron emission tomography (PET).

A conventional CT imaging device includes an x-ray source and an x-ray sensitive detector disposed on opposite sides of an examination region. A human patient or other object to be examined is supported in the examination region by a suitable support. The source emits x-ray radiation which transverses the examination region and is detected by the detector as the source and detector rotate about a center of rotation. A CT imaging device capable of having an offset detector geometry includes an x-ray source and an x-ray sensitive detector that may be transversely displaced from the center of rotation in the transaxial plane in certain configurations. Such offset detector geometry CT imaging devices are desirable because they allow for an increased field of view or allow for the use of a smaller sized detector.

However, if the detector of such an offset detector geometry CT imaging device does not span the full width of the imaged object, the projection data obtained is truncated. Artifacts, such as cone-beam and shading artifacts, are often introduced during the reconstruction of such truncated projection data. This is especially the case with asymmetric objects and objects that are not iso-centered.

Currently, two general approaches are known for the reconstruction of projection data obtained from CT imaging systems with offset detectors in the native cone-beam geometry. The first known approach is described in Ge Wang, *X-Ray Micro-CT With a Displaced Detector Array*, Med. Phys. 29(7), July 2002, pp. 1634-1636. According to the Wang method, redundancy weighting is applied to the measured line integrals before the truncated projection data is reconstructed using the Feldkamp-Davis-Kress (FDK) reconstruction algorithm or some other reconstruction algorithm.

A second conventional approach is described in Cho et al., *Cone-beam CT for Radiotherapy Applications*, Phys. Med. Biol. 40 (1995), pp. 1863-1883. According to this Cho et al. approach, the truncated projections are extended prior to the filtering step of the FDK algorithm by using projection data measured by the detector on the opposing side of the acquisition trajectory as estimated projection data and splicing it with the actual measured projection data to generate non-truncated projection data. After estimated non-truncated projection data is obtained in accordance with this Cho et al. method, the projection data is filtered. Redundancy weighting is then applied to the projection data after the filtering step and prior to back-projection in the FDK reconstruction algorithm. The redundancy weighting of this Cho et al. method removes the estimated projection data that was spliced with the actual measured projection data prior to the back-projection step.

It is desirable to provide a method and apparatus that more effectively reconstructs the projection data obtained from CT imaging devices with offset detector geometries and prevents or alleviates the artifacts that can typically occur during the reconstruction of such projection data.

Aspects of the present invention address these matters, and others.

According to one aspect of the present invention, a method and apparatus are provided to improve the reconstruction of projection data obtained from CT imaging devices with offset detector geometries. According to a particular aspect of the present invention, a method is provided including the following steps: (i) matching projection data measured at opposing sides of the acquisition trajectory and splicing them together to generate a full, non-truncated projection data set; (ii) differentiating the projection data; (iii) filtering the differentiated projection data with a filter, such as for example a Hilbert filter; (iv) applying redundancy weighting to the filtered projection data; and (v) back-projecting the redundancy weighted projection data to generate image data. In accordance with this aspect, the artifacts that typically occur with the reconstruction of imaging data obtained from CT imaging devices with offset detector geometries can be avoided or alleviated.

Still further aspects of the present invention will be appreciated by those of ordinary skill in the art upon reading and understanding the following detailed description. Numerous additional advantages and benefits will become apparent to those of ordinary skill in the art upon reading the following detailed description of preferred embodiments.

The invention may take form in various components and arrangements of components, and in various process operations and arrangements of process operations. The drawings are only for the purpose of illustrating preferred embodiments and are not to be construed as limiting the invention.

One aspect of the present invention is directed generally to a method and apparatus for CT image acquisition, and more particularly to a method and apparatus for reconstructing projection data obtained from CT imaging devices with offset detector geometries.

Figure 1A:
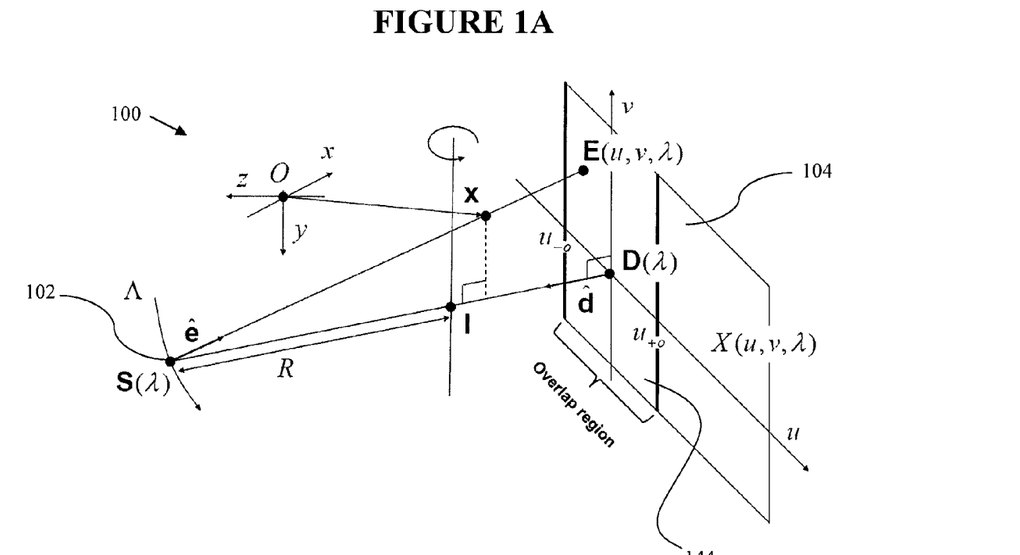
FIG. 1A is a schematic perspective view of an offset detector CT acquisition geometry according to an embodiment of the invention.

FIG. 1A depicts a perspective schematic view of an exemplary offset detector geometry 100. The exemplary offset detector geometry 100 has an x-ray source 102 and an x-ray sensitive detector 104 that are rotated around the y-axis. The distance between the source 102 and the detector 104 is designated D and the distance from the source 102 to the rotation axis is denoted by R. The iso-center of the imaging system is labeled I. The circular orbit is parameterized by the path length $\lambda \in \Lambda = [0, 2\pi R)$. The projected iso-center on the detector 104 is located at $D(\lambda)$ and defines the origin of the detector system. The detector 104 v-axis is parallel to the rotational axis and has an extent $v_{min} \leq v \leq v_{max}$. Accordingly, the μ-axis is parallel to the trajectory tangent vector with $\mu_{min} \leq \mu \leq \mu_{max}$. The cone beam projection data is denoted by $X(\mu,v,\lambda)$:

$$X(\mu,v,\lambda) = \int_0^\infty f(S(\lambda) + l\hat{e}(\mu,v,\lambda))dl,$$

where $\hat{e}(\mu,v,\lambda)$ is the unit vector from the source position $S(\lambda)$ to the detector element $E(\mu,v,\lambda)$. The corresponding length is denoted by $\overline{SE}$. The detector 104 is positioned in an off-center geometry. The overlap region $O(\lambda) = \{(\mu,v) \in \mathbb{R}^2 | \mu_{-0} \leq \mu \leq \mu_{+0}, v_{min} \leq v \leq v_{max}\}$ of the detector 104 is defined as the symmetric region around $D(\lambda)$ with measured projection values $X(\mu,v,\lambda)$. The width of the overlap region is $\Delta\mu = \mu_{+0} - \mu_{-0}$.

Figure 1B:
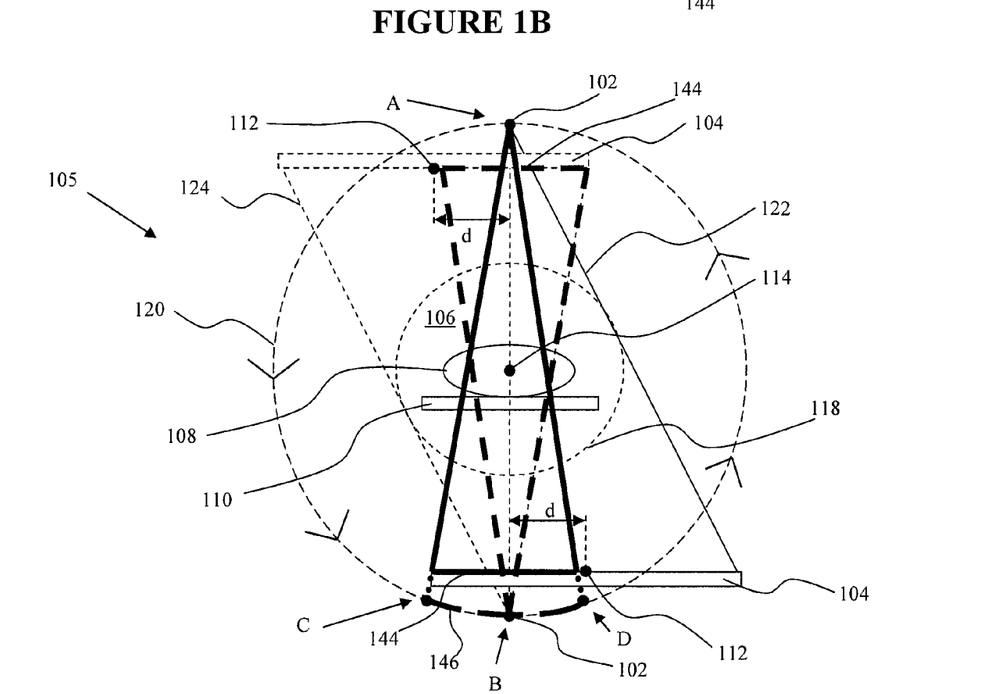
FIG. 1B is a transaxial view of an offset detector CT acquisition geometry according to an embodiment of the invention with the source and detector illustrated in opposite positions.

FIG. 1B depicts a transaxial view of an exemplary offset detector geometry 105 for an imaging apparatus. As with the offset acquisition geometry of FIG. 1A, the offset detector geometry 105 has an x-ray source 102, such as an x-ray tube, and an x-ray sensitive detector 104, such as a flat panel area detector array extending in the transverse and axial directions. An object support 110 supports the object 108 under examination in an examination region 106. The detector center 112 of the detector 104 of the exemplary offset detector geometry 105 is transversely displaced or offset from the center of rotation 114 in the transaxial plane by a distance "d".

The x-ray source 102 and the x-ray sensitive detector 104 rotate about the center of rotation 114. The source 102 and detector 104 are generally mounted to a rotating gantry (not shown) for rotation about the examination region 106. An exemplary acquisition trajectory 120 of the source 102 is illustrated by a dashed circle in FIG. 1B. In some embodiments, however, the source 102 and detector 104 may remain at a constant angular position while the object 108 is moved and/or rotated to produce the requisite angular sampling. As illustrated in FIG. 1B, the exemplary offset detector geometry 105 has a transverse field of view ("FOV") 118.

In FIG. 1B, the x-ray source 102 and detector 104 of the exemplary offset detector geometry 105 are depicted in two opposite positions in the transaxial plane, position A in solid lines and position B in dotted lines. In source position A as illustrated, the source 102 is disposed above the object 108 and the detector 104 is disposed below the object 108. In source position B, the x-ray source 102 and detector 104 are rotated 180 degrees about the center of rotation 114 from position A, so the source is disposed below the object 108. As illustrated in FIG. 1B, the detector center 112 is offset from the center of rotation 114 in the transaxial plane by a distance "d" in both positions.

As illustrated in FIG. 1B, the source 102 generates a cone 122 of radiation in source position A and a cone 124 of radiation in source position B. When the source 102 is on an arc segment 146 of the acquisition trajectory 120 from source position C to source position D, the detector 104 measures redundant projection data to source position A. The area 144 of the detector 104 that receives overlapping or redundant radiation is shown in bold lines in FIG. 1B. The overlap area 144 remains in the same location relative to the detector center 112 as the detector 104 rotates about the center of rotation 114. The term "redundant ray," "redundancy" or "redundant" will be used in the following also for rays not included in the plane of a circular rotation, i.e. for rays with the same cone angle elevation and an identical projection in the plane of rotation. For circular acquisition trajectories this projection data is not identical due to the divergent geometry.

The amount of overlap may be varied by varying the distance "d" between the detector center 112 and the center of rotation 114. This overlap area 144 may be optimized based on various factors, such as the estimated size of the object 108 under examination, the scan protocol, and other factors. However, increasing the amount of overlap decreases the size of the transverse FOV 118. Thus, decreasing the distance "d" increases the amount of overlap and decreases the size of the transverse FOV 118. Conversely, increasing the distance "d" decreases the amount of overlap and increases the size of the transverse FOV 118.

Maximum overlap of the radiation occurs at full beam geometry. Full beam geometry corresponds to the situation where the detector center 112 of the detector 104 intersects the transverse center of rotation 114 (i.e., where "d"=0). There is zero overlap of the radiation when the distance "d" is equal to or greater than the width of one half of the detector 104. Zero overlap provides for a maximum size of the transverse FOV 118. Further, in a zero overlap configuration, a rotation of approximately 360 degrees is needed to obtain a complete angular sampling. On the other hand, a rotation of 180 degrees plus the fan or cone angle provides a complete angular sampling when configured in the full beam geometry, assuming the detector 104 is wide enough to span the entire object 108 in the transaxial plane of FIG. 1B. The requisite angular range for intermediate configurations varies between 180 degrees plus the fan angle and 360 degrees, and can readily be calculated from the geometry of the system 105.

While the figures and the description are focused on the use of flat panel detectors, arcuate detectors or detectors having yet other shapes may also be used. Furthermore, while the figures and the description focus on a CT system in which the source 102 is a point source, other alternatives are contemplated. For example, the source 102 may be a line source. Gamma and other radiation sources may also be used. Multiple sources 102 and detectors 104 may also be provided, in which case corresponding sets of sources and detectors may be offset angularly and/or longitudinally from one another.

The detector center 112 may be offset from the center of rotation 114 in the transaxial plane by various distances "d" in different embodiments of the present invention. The detector 104 may be shifted to vary the size of the transverse FOV 118 by any suitable means. For example, the detector 104 may be moved in various directions relative to the rotating gantry and the center of rotation 114 either manually by a human user or by a mechanical drive. It can be shifted linearly, as is useful with a flat panel detector, or rotationally, as is useful for a curved detector. While the exemplary offset detector geometry 105 described includes a centered source and an offset detector, it should be understood that additional CT imaging device geometries, which include an offset source or an offset source and an offset detector are contemplated.

Figure 2:
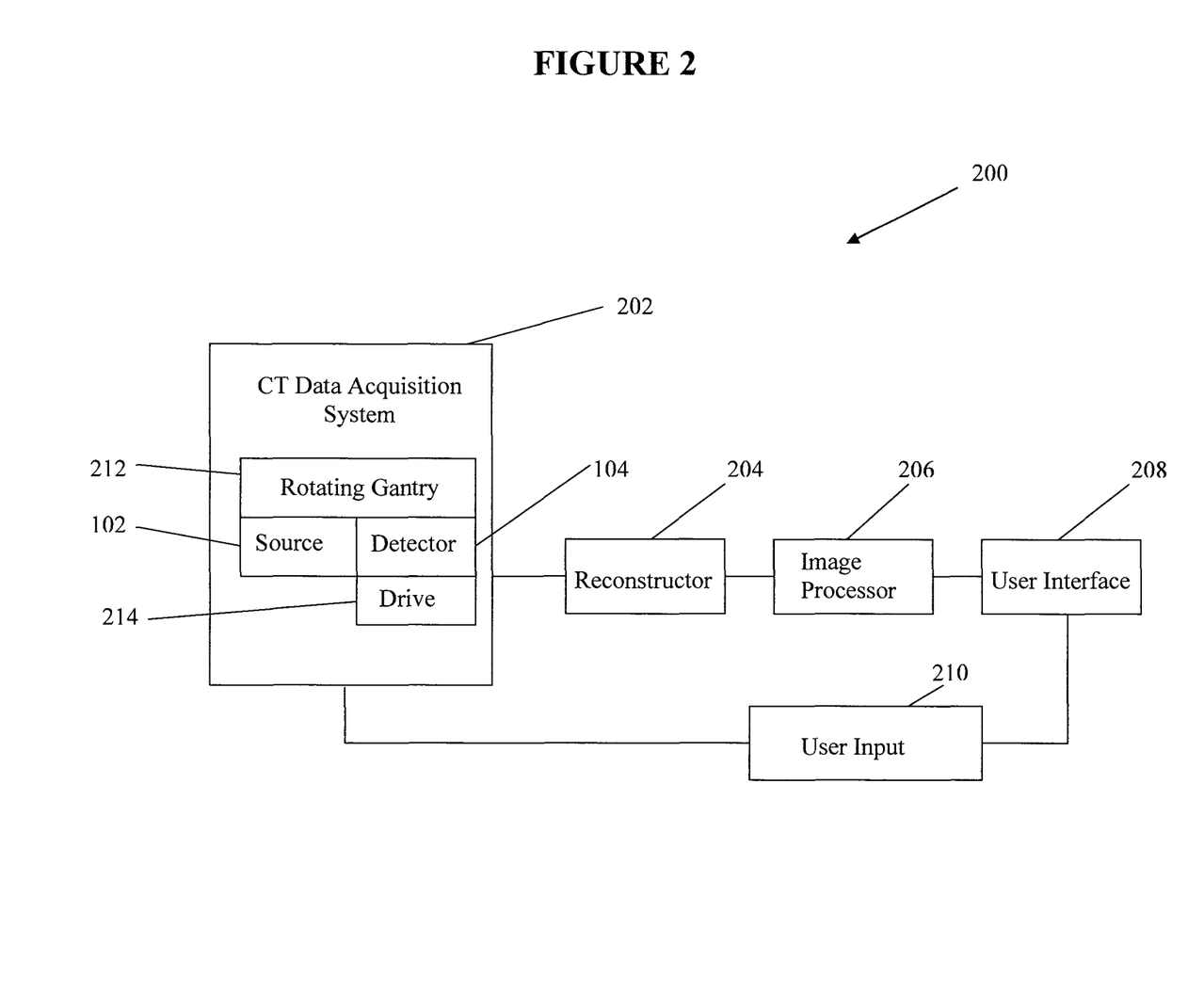
FIG. 2 is an imaging system according to an embodiment of the invention.

FIG. 2 depicts a CT imaging system 200 suitable for use with the exemplary offset detector geometry 105 described above. The CT imaging system 200 includes a CT data acquisition system 202, a reconstructor 204, an image processor 206, a user interface 208, and a user input 210. The CT data acquisition system 202 includes the source 102 and detector 104, which are mounted to a rotating gantry 212 for rotation about the examination region. Circular or other angular sampling ranges as well as axial, helical, circle and line, saddle, or other desired scanning trajectories are contemplated. The embodiment of the CT imaging device system 200 illustrated in FIG. 2 includes a drive 214, such as a microstep motor, that provides the requisite force required to move the source 102 and/or detector 104.

The reconstructor 204 reconstructs the data generated by the data acquisition system 202 using reconstruction techniques to generate volumetric data indicative of the imaged subject. The image processor 206 processes the volumetric data as required, for example for display in a desired fashion on the user interface 208, which may include one or more output devices such as a monitor and printer.

The user interface 208, which is advantageously implemented using software instructions executed by a general purpose or other computer so as to provide a graphical user interface ("GUI"), allows the user to control or otherwise interact with the imaging system 200, for example by selecting a desired FOV configuration or dimension, initiating and/or terminating scans, selecting desired scan or reconstruction protocols, manipulating the volumetric data, and the like.

A user input 210 operatively connected to the user interface 208 controls the operation of the CT data acquisition system 202, for example to carry out a desired scanning protocol, optionally position the detector 104 and/or the source 102 so as to provide the desired FOV, and the like.

As previously described, the projection data obtained from CT imaging systems with offset detectors will be truncated if the detector does not span the full width of the imaged object. For example, as illustrated in FIG. 1B, slightly more than half of a patient's torso or other imaged object may be imaged in each projection. The filtered back-projection reconstruction of such truncated projection data can introduce strong cone-beam and shading artifacts, especially for asymmetric imaged objects or imaged objects that are not perfectly iso-centered. This is due to the fact that high-pass filtering of an abrupt truncation edge, where zeros are substituted for the missing data, enhances high frequency components and produces artifacts.

Figure 3:
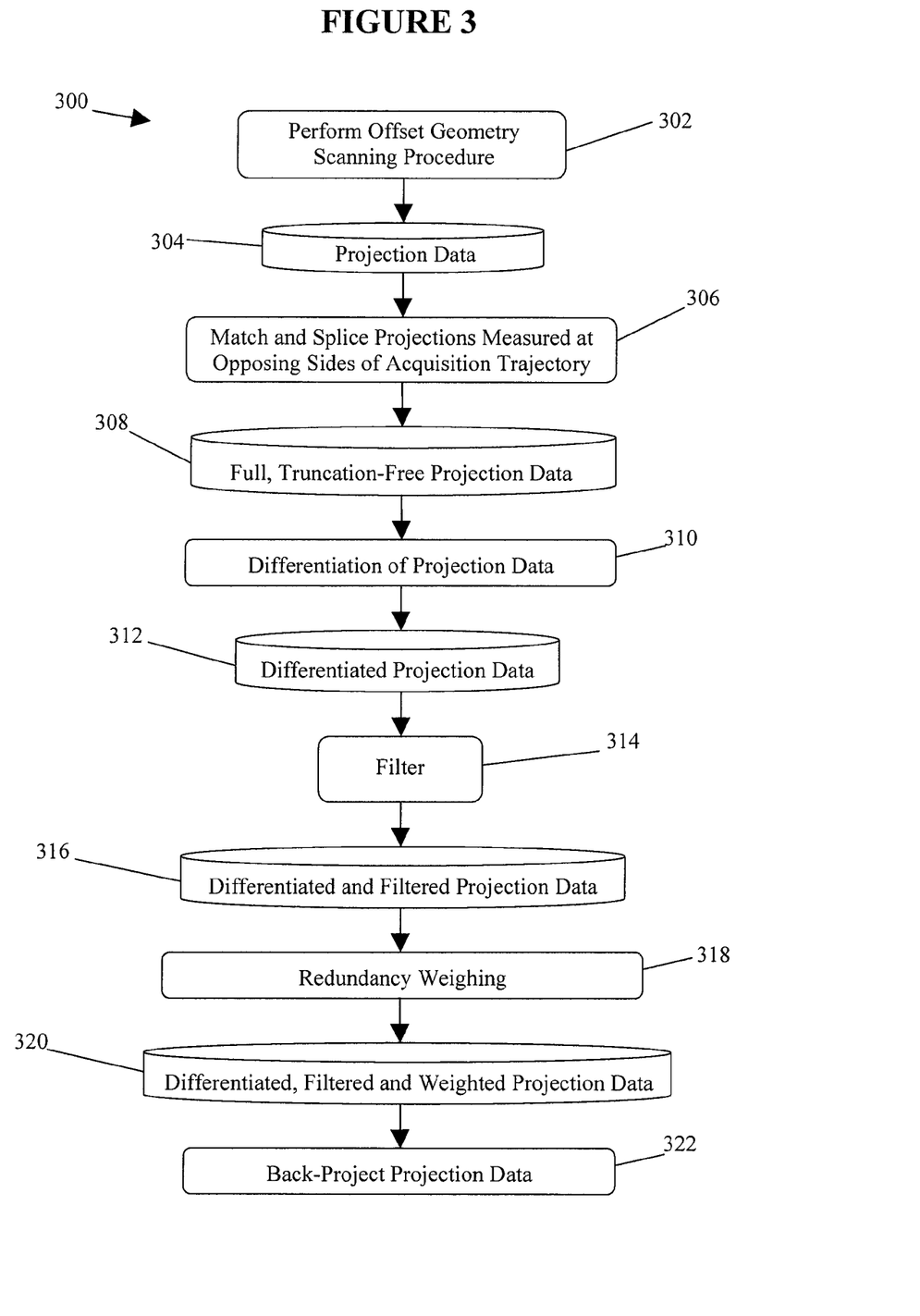
FIG. 3 depicts an image reconstruction method according to an embodiment of the invention.

An exemplary image reconstruction process 300 according to one aspect of the present invention is illustrated in FIG. 3. The exemplary process 300 reconstructs projection data obtained from a CT imaging device with an offset detector geometry more effectively than either the Wang method or the Cho et al. method. In step 302, the CT imaging system 200 is utilized to take scans of the imaged object with the source 102 and detector 104 in the exemplary offset detector geometry 105. In this step, projection data 304 of the imaged subject 108 is acquired at a sufficient plurality of angular positions about the examination region 106 for a desired image resolution. As previously described, the projection data 304 obtained from a CT imaging system 200 with the exemplary offset detector geometry 105 will be truncated if the detector 104 does not span the full width of the imaged object 108 in the transaxial plane.

Figure 4:
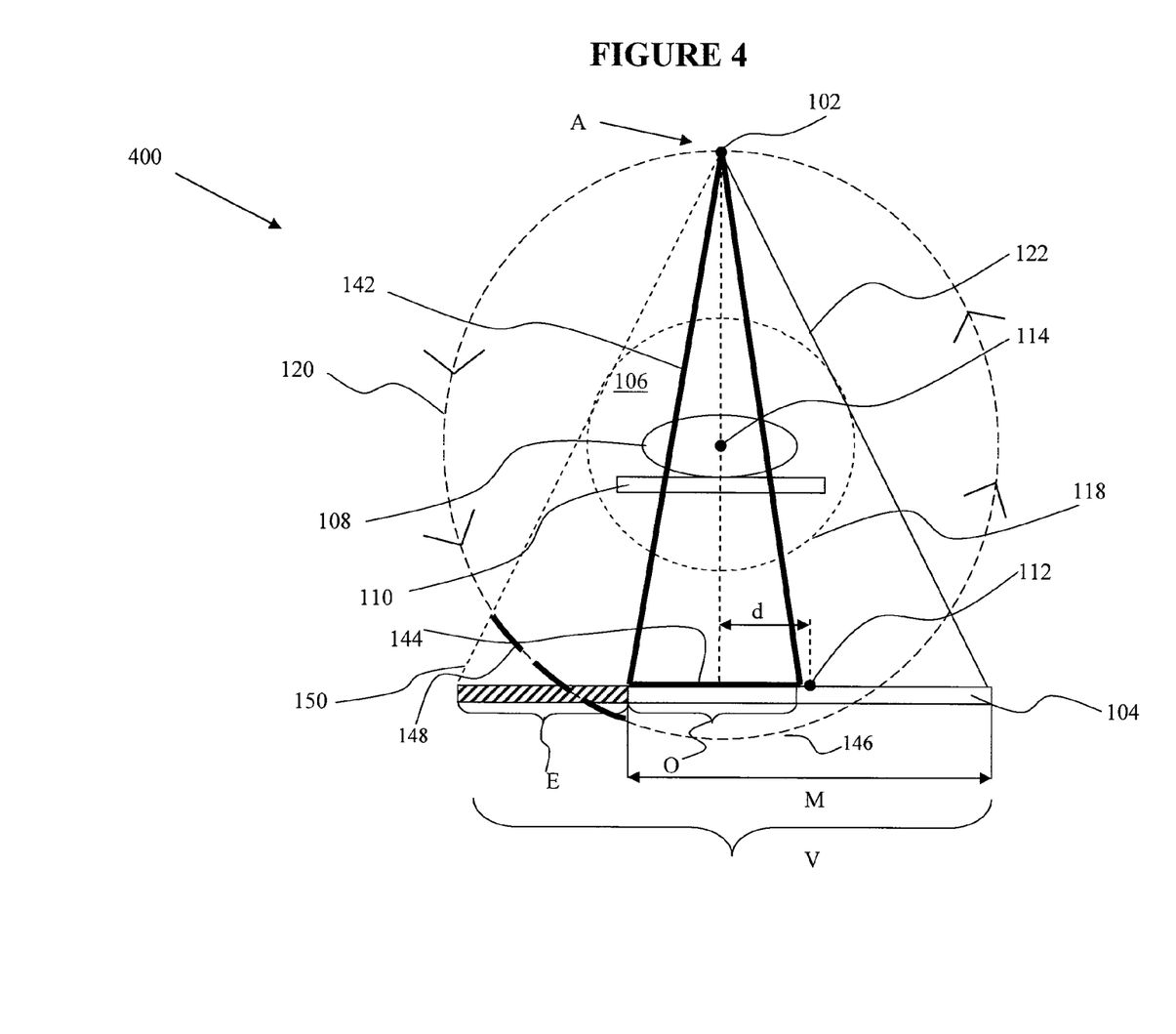
FIG. 4 is a transaxial view of an offset detector CT acquisition geometry according to an embodiment of the invention illustrating the matching and splicing together of projection data obtained from opposing locations on an acquisition trajectory to generate full, non-truncated projection data.
Figure 5A:
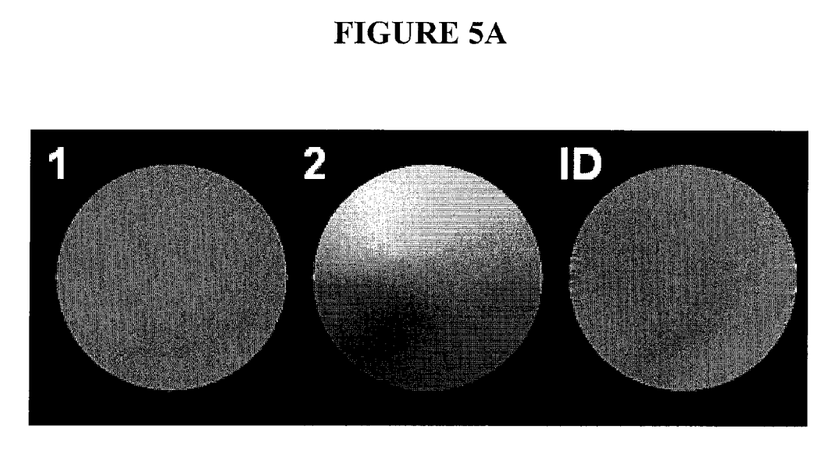
FIG. 5A is an exemplary reconstructed image generated by a software program of a simulated homogenous ball with a diameter of 200 mm positioned 40 mm off iso-center with a 66 mm detector overlap taken along the central axial plane, L/W 0/105 HU, with image 1 being reconstructed in accordance with the Wang method, image 2 being reconstructed in accordance with the Cho et al. method, and image ID being reconstructed in accordance with an embodiment of the present invention.
Figure 5B:
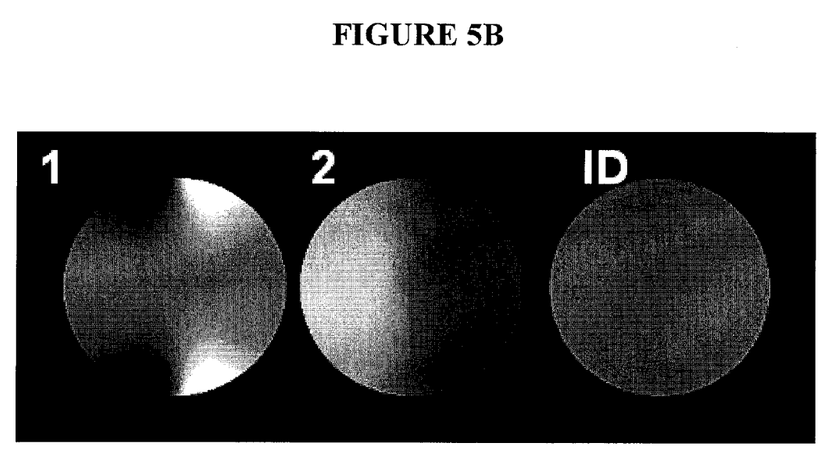
FIG. 5B is an exemplary reconstructed image generated by a software program of the same simulated homogenous ball as in FIG. 5A, except taken along the central sagittal plane, with image 1 being reconstructed in accordance with the Wang method, image 2 being reconstructed in accordance with the Cho et al. method, and image ID being reconstructed in accordance with an embodiment of the present invention.
Figure 6A:
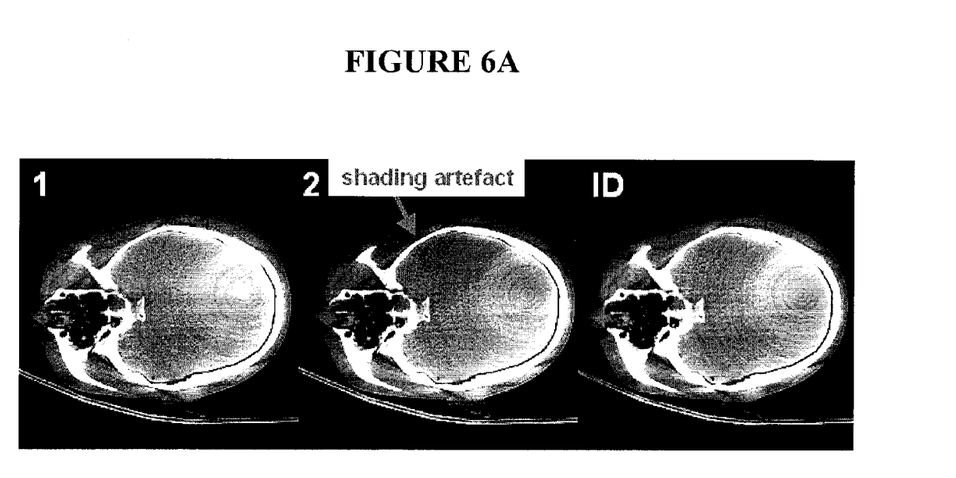
FIG. 6A is an exemplary reconstructed image generated by a software program of a head phantom positioned about 60 mm off iso-center with a 20 mm detector overlap taken along the central axial plane, L/W 0/200 HU, with image 1 being reconstructed in accordance with the Wang method, image 2 being reconstructed in accordance with the Cho et al. method, and image ID being reconstructed in accordance with an embodiment of the present invention.
Figure 6B:
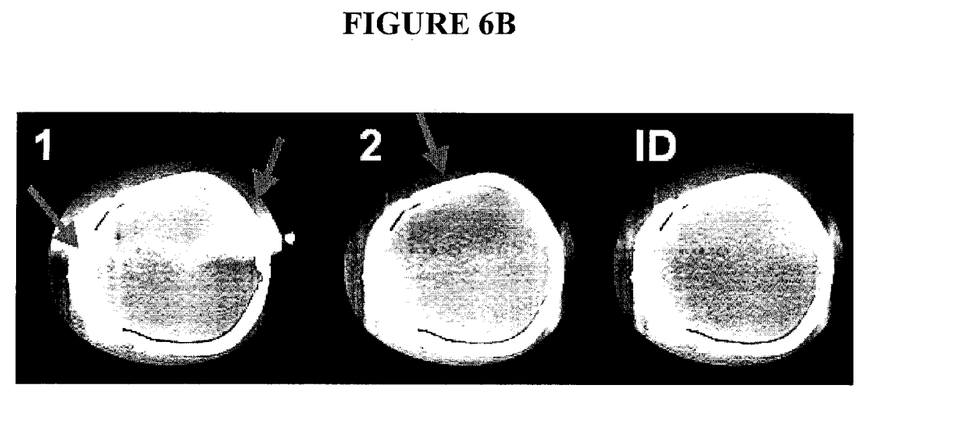
FIG. 6B is an exemplary reconstructed image generated by a software program of a head phantom as in FIG. 6A, except taken along the central sagittal plane, with image 1 being reconstructed in accordance with the Wang method, image 2 being reconstructed in accordance with the Cho et al. method, and image ID being reconstructed in accordance with an embodiment of the present invention.

In step 306, projection data from two or more projections measured by the detector 104 at opposing sides of the acquisition trajectory 120 are matched and then spliced together to generate estimated, non-truncated projection data 308. As a way of illustrating step 306, FIG. 4 depicts the x-ray source 102 and detector 104 of the exemplary offset detector geometry 105 position A of FIG. 1B. As can be seen in FIGS. 1B and 4, the position A projection does not fully encompass the object 108. Rather, a small left portion of the object 108 (from the viewpoint shown in the FIGURES) is not covered. Data gathered by the source 102 and the detector 104 when the source 102 is disposed opposed to position A and on the arc segment 148 may be used to estimate the missing projection data E in source position A. That estimate may then be spliced together with the projection data actually measured by the detector 104 in position A.

For example, the truncated projection data can be rebinned to a non-truncated projection data set using complementary rays from the opposing side of the acquisition trajectory 120. Referring again to FIG. 1A, the fan angle α of a specific ray μ is given by $\alpha(\mu)=\text{atan}(\mu/D)$ and the source angle by $\beta-\lambda/R$. Rewriting the projection data with these coordinates gives: $X(\alpha,v,\beta)=X(\text{atan}(\mu/D),v,\lambda/R)$. The truncated projections can be spliced with projection data from complementary rays in the region $\mu_{min} \leq \mu \leq \mu_{-0}$ with $\mu_{min}=-\mu_{max}$:

$$\tilde{X}_1(\alpha,v,\beta)=\tilde{X}(-\alpha,v,\beta\pm 2\alpha+\pi) \text{ for } \alpha(\mu_{min})\leq\alpha\leq\alpha(\mu_{-0})$$

where the sign depends on the rotation direction of the source 102. The estimated projection data might be alternatively generated as an approximation from a single view with the source 102 at source position B or any other discrete location along arc 146 or 148.

To achieve a smooth transition between the spliced projection data and the originally measured projection data, a faded additive offset correction can be optionally applied. Switching back to the detector coordinates gives:

$$X_2(u,v,\lambda) = \begin{cases} X_1(u,v,\lambda), & u_{min} \leq u < (u_{-0}-\Delta) \\ X_1(u,v,\lambda)+\delta\cos\left(\frac{\pi}{2}\frac{u_{-0}-u}{\Delta}\right), & (u_{-0}-\Delta) \leq u \leq u_{-0} \\ X(u,v,\lambda), & u_{-0} < u \leq u_{max}, \end{cases}$$

where $\delta=X(\mu_{-0},v,\lambda)-X_1(\mu_{-0},v,\lambda)$ defines the offset and the fading region is chosen as $\Delta=\mu_{+0}-\mu_{-0}$.

In this manner, an estimated and truncation free projection data set is generated, which includes projection data for the entire imaged object 108. The splicing together of the projection data mimics a virtual detector V shown in FIG. 4 that spans the entire imaged object 108 and corresponds to a virtual cone of radiation 150 illustrated in FIG. 4. The area of the virtual detector V that is generated from actual projection data measured by the detector 104 in position A is designated "M." The area of the virtual detector V that is estimated from the projection data measured by the detector 104 when the source 102 travels along arc 148 or when the source 102 is located in any discrete position on arc 148, is designated "E." Position A of the source 102 and detector 104 shown in FIG. 4 is merely an exemplary position used to illustrate the matching and splicing together of projection data of step 306. Any position on the acquisition trajectory 120 could be used for this procedure. For example, every projection taken in the acquisition trajectory 120 could be matched and spliced together with a projection or projections taken at an opposing side of the acquisition trajectory 120 in certain embodiments. In additional embodiments, only a portion of the projections could be matched and spliced together.

As discussed above with respect to FIG. 1B, the area 144 (shown in bold lines) of the detector 104 receives overlapping or redundant radiation in opposing positions. This area of the detector that gathers redundant or overlapping projection data in opposing positions is illustrated as area O of virtual detector V in FIG. 4.

Returning to FIG. 3, the substitution of estimated projection data for the missing projection data results in a full, non-truncated projection data 308. The full, non-truncated projection data 308 is differentiated in step 310 with respect to the acquisition trajectory 120 to generate differentiated projection data 312. During the differentiation step 310, neighboring rays measured with the source 102 at different positions along the acquisition trajectory 120 that have the same fan angle are differentiated. Such view-dependent data differentiation is disclosed by Noo et al., *A New Scheme for View-Dependent Data Differentiation in Fan-Beam and Cone-Beam Computed Tomography*, Phys. Med. Biol. 52 (2007), pp. 5393-5414, which is fully incorporated herein by reference.

In step 314, a filter such as for example a Hilbert filter or a modified Hilbert filter is applied to the differentiated projection data 312 to generate differentiated and filtered projection data 316. The differentiation step 310 and the filtering step 314 cumulatively serve as a two-step filtering step.

Redundancy weighting is applied to the differentiated and filtered projection data 316 at step 318 to generate differentiated, filtered and weighted projection data 320. The fact that the redundancy weighting is applied after filtering 314 as opposed to being applied prior to filtering 314 is advantageous because it increases the effectiveness of the filtering. The redundancy weighting is restricted to the overlap region resulting in a rather steep transition from measured data to zero. The high-pass filtering of the projection incorporated in the filtered back-projection amplifies any kind of data inconsistency (e.g. scattered X-ray radiation, geometry jitter, cone beam approximation, etc.) of the data that is expected to be redundant. Therefore, filtering the full, non-truncated, smooth profile and applying redundancy weighting after filtering is much less sensitive to any kind of imperfections in the data. The two-step filtering of this detailed description achieved by the differentiation step 310 and the filtering step 314 provides for such an application of redundancy weighting after filtering.

Since some points of the imaged object 108 are doubly scanned due to the redundancy of the projection data measured by the detector 104 in opposing positions of the acquisition trajectory 120 (such as illustrated by section O of the virtual detector V of FIG. 4), a redundancy weight is attached to these overlapping pixels. A variety of different known weighting functions can be utilized to assign weights to the redundant or overlapping pixels in the differentiated and filtered projection data 316. The weighting preferably ensures that the summed contribution of each pair of redundant rays equals one. For example, the redundancy weighting functions proposed by Parker (*Optimal Short Scan Convolution Reconstruction for Fanbeam CT*, Med. Phys. 9(2), March/April 1982, pp. 254-257) or Cho et al. discussed above could be employed. For example, a redundancy weight $\omega(\mu)$ can be introduced according to:

$$\omega(u) = \begin{cases} 0, & u_{min} \leq u < u_{-0} \\ \sin^2\left(\frac{\pi}{2}\frac{u-u_{-0}}{\Delta u}\right), & u_{-0} \leq u \leq u_{+0} \\ 1, & u_{+0} < u \leq u_{max} \end{cases}$$

During the redundancy weighting step 318, a weight of zero is attached to the estimated projection data spliced to the actual projection data. It is useful to remove the estimated projection data from the differentiated and filtered projection data 316 prior to back-projection to prevent artifacts from being introduced by the back-projection of the estimated projection data. To minimize artifacts, only data from actually measured pixel locations is back-projected. Essentially, the estimated projection data is preferably used for the differentiation step 310 and the filtering step 314, and then discarded.

In step 322, the differentiated, filtered and weighted projection data 320 is back-projected by the reconstructor 204 using conventional back-projection, such as distance weighted back-projection or other back-projection algorithms, to generate volumetric data indicative of the imaged subject 108. The image processor 206 may then processes the volumetric data as required, for example for display in a desired fashion on the user interface 208.

Problems associated with the incorrect handling of redundant data can be alleviated by the use of an algorithm that applies redundancy weighting after the filtering step. Applying redundancy weighting after filtering can be accomplished in a variety of different ways. For example, this can either be achieved by rebinning to parallel geometry with subsequent standard filtered back projection (FBP) or by applying a Katsevich-style algorithm to the circular acquisition data. For example, the following Katsevich-style algorithm could be used:

$$f_{new}(x) = \frac{1}{2\pi}\int_\Lambda \frac{\omega(u)}{R(x-I)\cdot\hat{d}}\int_{-\infty}^{\infty}\frac{D}{SE(x)}X_d(u',v,\lambda)h_H(u-u')du'(1/R)\,d\lambda,$$

with $$h_H(\rho) = -\int_{-\infty}^{\infty} i\,\text{sgn}(P)e^{j2\pi\rho P}dP, \text{ and}$$

$$X_d(u,v,\lambda) = \left(\frac{\partial\chi_2}{\partial\lambda} + \frac{\partial\chi_2}{\partial u}\frac{\partial u}{\partial\lambda} + \frac{\partial\chi_2}{\partial v}\frac{\partial v}{\partial\lambda}\right)(u,v,\lambda)$$

is the derivative along the source trajectory with fixed ray direction. This derivative can be computed using the blended chain rule for arbitrary detector orientations derived by Noo et al. cited above. In the central plane, this algorithm reduces to the fan-beam algorithm proposed by Noo et al., *Image Reconstruction from Fan-Beam Projections on Less Than a Short Scan*, Phys. Med. Biol. 47 (2002), pp. 2525-2546. Note, that the generalized 3D variant of Noo et al.'s 2D fan-beam algorithm proposed by Yu et al., *Feldkamp-type VOI Reconstruction from Super-Short-Scan Cone Beam Data*, Med. Phys. 31(6), June 2004, pp. 1357-1362, differs slightly by applying the cone angle weighting before the differentiation step instead of after it.

Referring now to FIGS. 5A, 5B, 6A and 6B, exemplary reconstructed images reconstructed in accordance with the Wang method, the Cho et al. method and an embodiment of the present invention are illustrated. In FIGS. 5A, 5B, 6A and 6B, the images labeled as 1 were reconstructed in accordance with the Wang method, the images labeled as 2 were reconstructed in accordance with the Cho et al. method, and the images labeled as "ID" were reconstructed in accordance with an embodiment of the present invention. The images reconstructed in accordance with the Wang method and Cho et al. method exhibit artifacts, identified for example by the arrows in FIGS. 6A and 6B. The images reconstructed in accordance with an embodiment of the present invention illustrate the greater effectiveness of the embodiment of the present invention in reducing such artifacts.

The aforementioned functions, such as for example, selecting a desired FOV configuration or dimension, initiating and/or terminating scans, selecting desired scan or reconstruction protocols, manipulating the volumetric data, and the like, can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic, databases or tables shown and described herein preferably reside in or on a computer readable medium, such as a component of the imaging system 200 like the reconstructor 204 or the image processor 206. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An imaging method, comprising the steps of:
acquiring projection data of an object with an imaging apparatus comprising a detector which is offset from a center of rotation;
matching at least one first projection from the projection data with at least one second projection from the projection data, wherein the at least one second projection is measured at an approximately opposing side of an acquisition trajectory from the at least one first projection;
splicing estimated projection data derived from the projection data of the at least one second projection with projection data of the first projection to generate a full, non-truncated projection data set;
differentiating the non-truncated projection data set with respect to the acquisition trajectory to generate differentiated projection data;
applying a filter to the differentiated projection data to generate differentiated and filtered projection data;
applying redundancy weighting to the differentiated and filtered projection data to generate differentiated, filtered and weighted projection data; and
back-projecting the differentiated, filtered and weighted projection data to generate volumetric data indicative of the object;
wherein the at least one second projection is selected in a region $\mu_{min} \leq \mu \leq \mu_{-0}$ with $\mu_{min} = -\mu_{max}$ according to $\tilde{X}_1(\alpha, v, \beta) = \tilde{X}(-\alpha, v, \beta + 2\alpha + \pi)$ for $\alpha(\mu_{min}) \leq \alpha \leq \alpha(\mu_{-0})$; and
wherein $\tilde{X}(\alpha, v, \beta) = X(\operatorname{atan}(\mu/D), v, \lambda/R)$, D is a distance from a source to the detector, R is a distance from the source to a rotation axis, a circular orbit is parameterized by a path length $\lambda \in \Lambda = [0, 2\pi R)$, a detector v-axis is parallel to the rotational axis, and a u-axis is parallel to a trajectory tangent vector.

2. The method of claim 1, wherein the non-truncated projection data set corresponds to a virtual projection measured by a single virtual detector capable of spanning the imaged object.

3. The method of claim 1, wherein the redundancy weighting is applied to pixels of the differentiated and filtered projection data that were redundantly measured by the first projection and the at least one second projection at the approximately opposing sides of the acquisition trajectory.

4. The method of claim 1, wherein the redundancy weighting comprises applying a weight of zero to the estimated projection data spliced from the at least one second projection.

5. The method of claim 1, wherein the redundancy weighting comprises applying a redundancy weight $\omega(\mu)$ according to:

$$\omega(u) = \begin{cases} 0, & u_{min} \leq u < u_{-0} \\ \sin^2\left(\frac{\pi}{2}\frac{u - u_{-0}}{\Delta u}\right), & u_{-0} \leq u \leq u_{+0} \\ 1, & u_{+0} < u \leq u_{max}. \end{cases}$$

6. The method of claim 1, wherein the filter is a Hilbert filter or a modified Hilbert filter.

7. The method of claim 1, wherein the imaging method comprises a reconstruction algorithm according to:

$$f_{new}(x) = \frac{1}{2\pi} \int_\Lambda \frac{\omega(u)}{R-(x-I)\cdot \hat{d}} \int_{-\infty}^\infty \frac{D}{\overline{SE}(x)} X_d(u', v, \lambda) h_H(u-u') du' (1/R) d\lambda,$$

with $$h_H(\rho) = -\int_{-\infty}^\infty i \operatorname{sgn}(P) e^{j2\pi\rho P} dP, \text{ and}$$

$$X_d(u, v, \lambda) = \left(\frac{\partial \chi_2}{\partial \lambda} + \frac{\partial \chi_2}{\partial u}\frac{\partial u}{\partial \lambda} + \frac{\partial \chi_2}{\partial v}\frac{\partial v}{\partial \lambda}\right)(u, v, \lambda);$$

wherein I is an iso-center of the imaging apparatus, the detector center is offset from the center of rotation in a transaxial plane by a distance d, and $\overline{SE}$ is a length from the source to a detector element.

8. The method of claim 1, wherein the imaging apparatus is a cone-beam computed tomography imaging device.

9. An apparatus for acquiring projection data at a plurality of angular positions relative to an object disposed in an examination region, the apparatus comprising:
a radiation source;
a radiation sensitive detector which detects radiation emitted by the source that has traversed the examination region, wherein the detector is offset from a center of rotation; and
a reconstructor;
wherein the apparatus is adapted to perform a scanning procedure of the object to obtain projection data;
wherein at least one first projection from the projection data is matched with at least one second projection from the projection data, wherein the at least one second projection is measured at an approximately opposing side of an acquisition trajectory from the at least one first projection;
wherein projection data from the at least one second projection is used to derive estimated projection data that is spliced with projection data of the first projection to generate a full, non-truncated projection data set;
wherein the full, non-truncated projection data set is then differentiated with respect to the acquisition trajectory to generate differentiated projection data;
wherein the differentiated projection data is then filtered to generate differentiated and filtered projection data;
wherein redundancy weighting is applied to the differentiated and filtered projection data to generate differentiated, filtered and weighted projection data;
wherein the differentiated, filtered and weighted projection data is then back-projected by the reconstructor to generate volumetric data indicative of the object; and
wherein the at least one second projection is selected in a region $\mu_{min} \leq \mu \leq \mu_{-0}$ with $\mu_{min} = -\mu_{max}$ according to $\tilde{X}_1(\alpha, v, \beta) = \tilde{X}(-\alpha, v, \beta + 2\alpha + \pi)$ for $\alpha(\mu_{min}) \leq \alpha \leq \alpha(\mu_{-0})$; and
wherein $\tilde{X}(\alpha, v, \beta) = X(\operatorname{atan}(\mu/D), v, \lambda/R)$, D is a distance from a source to the detector, R is a distance from the source to a rotation axis, a circular orbit is parameterized by a path length $\lambda \in \Lambda = [0, 2\pi R)$, a detector v-axis is parallel to the rotational axis, and a $\mu$-axis is parallel to a trajectory tangent vector.

10. The apparatus of claim 9, wherein the full, non-truncated projection data set corresponds to a virtual projection measured by a single virtual detector capable of spanning the imaged object.

11. The apparatus of claim 9, wherein the redundancy weighting is applied to pixels of the differentiated and filtered projection data that were redundantly measured by the first projection and the at least one second projection at the approximately opposing sides of the acquisition trajectory.

12. The apparatus of claim 9, wherein the redundancy weighting comprises applying a weight of zero to the estimated projection data spliced from the at least one second projection.

13. The apparatus of claim 9, wherein the redundancy weighting comprises applying a redundancy weight $\omega(\mu)$ according to:

$$\omega(u) = \begin{cases} 0, & u_{min} \leq u < u_{-0} \\ \sin^2\left(\frac{\pi}{2}\frac{u-u_{-0}}{\Delta u}\right), & u_{-0} \leq u \leq u_{+0} \\ 1, & u_{+0} < u \leq u_{max}. \end{cases}$$

14. The apparatus of claim 10, wherein the filter is a Hilbert filter or a modified Hilbert filter.

15. The apparatus of claim 9, wherein the radiation sensitive detector is a flat detector.

16. The apparatus of claim 9, wherein the apparatus is a cone-beam computed tomography imaging device.

17. The apparatus of claim 9, further comprising a mechanical drive for moving the radiation sensitive detector with respect to the radiation source.

18. The apparatus of claim 9, further comprising an image processor, a user interface and a user input, and wherein the image processor processes the volumetric data for display on the user interface.

19. The apparatus of claim 9, wherein the reconstructor applies a reconstruction algorithm according to:

$$f_{new}(x) = \frac{1}{2\pi} \int_\Lambda \frac{\omega(u)}{R-(x-I)\cdot \hat{d}}$$
$$\int_{-\infty}^\infty \frac{D}{\overline{SE}(x)} X_d(u', v, \lambda) h_H(u-u') du' (1/R) d\lambda,$$

with $$h_H(\rho) = -\int_{-\infty}^\infty i \operatorname{sgn}(P) e^{j2\pi\rho P} dP, \text{ and}$$

$$X_d(u, v, \lambda) = \left(\frac{\partial \chi_2}{\partial \lambda} + \frac{\partial \chi_2}{\partial u}\frac{\partial u}{\partial \lambda} + \frac{\partial \chi_2}{\partial v}\frac{\partial v}{\partial \lambda}\right)(u, v, \lambda);$$

wherein I is an iso-center of the imaging apparatus, the detector center is offset from the center of rotation in a transaxial plane by a distance d, and $\overline{SE}$ is a length from the source to a detector element.

20. An imaging method, comprising the steps of:
acquiring projection data of an object with an imaging apparatus comprising a detector which is offset from a center of rotation;
matching at least one first projection from the projection data with at least one second projection from the projection data, wherein the at least one second projection is measured at an approximately opposing side of an acquisition trajectory from the at least one first projection;
splicing estimated projection data derived from the projection data of the at least one second projection with projection data of the first projection to generate a full, non-truncated projection data set;

differentiating the non-truncated projection data set with respect to the acquisition trajectory to generate differentiated projection data;

applying a filter to the differentiated projection data to generate differentiated and filtered projection data;

applying redundancy weighting to the differentiated and filtered projection data to generate differentiated, filtered and weighted projection data; and back-projecting the differentiated, filtered and weighted projection data to generate volumetric data indicative of the object;

wherein the redundancy weighting comprises applying a redundancy weight $\omega(\mu)$ according to:

$$\omega(u) = \begin{cases} 0, & u_{min} \leq u < u_{-0} \\ \sin^2\left(\frac{\pi}{2}\frac{u-u_{-0}}{\Delta u}\right), & u_{-0} \leq u \leq u_{+0}; \\ 1, & u_{+0} < u \leq u_{max} \end{cases} \text{ and}$$

wherein a $\mu$-axis is parallel to a trajectory tangent vector.

21. An imaging method, comprising the steps of:

acquiring projection data of an object with an imaging apparatus comprising a detector which is offset from a center of rotation;

matching at least one first projection from the projection data with at least one second projection from the projection data, wherein the at least one second projection is measured at an approximately opposing side of an acquisition trajectory from the at least one first projection;

splicing estimated projection data derived from the projection data of the at least one second projection with projection data of the first projection to generate a full, non-truncated projection data set;

differentiating the non-truncated projection data set with respect to the acquisition trajectory to generate differentiated projection data;

applying a filter to the differentiated projection data to generate differentiated and filtered projection data;

applying redundancy weighting to the differentiated and filtered projection data to generate differentiated, filtered and weighted projection data; and back-projecting the differentiated, filtered and weighted projection data to generate volumetric data indicative of the object;

wherein the imaging method comprises a reconstruction algorithm according to:

$$f_{new}(x) = \frac{1}{2\pi}\int_\Lambda \frac{\omega(u)}{R-(x-I)\cdot\hat{a}} \int_{-\infty}^{\infty} \frac{D}{\overline{SE}(x)}$$

$$X_d(u', \upsilon, \lambda) h_H(u-u') du' (1/R) d\lambda,$$

with $$h_H(\rho) = -\int_{-\infty}^{\infty} i \operatorname{sgn}(P) e^{j2\pi\rho P} dP,$$

and $$X_d(u, \upsilon, \lambda) = \left(\frac{\partial \chi_2}{\partial \lambda} + \frac{\partial \chi_2}{\partial u}\frac{\partial u}{\partial \lambda} + \frac{\partial \chi_2}{\partial \upsilon}\frac{\partial \upsilon}{\partial \lambda}\right)(u, \upsilon, \lambda);$$

wherein D is a distance from a source to the detector, R is a distance from the source to a rotation axis, a circular orbit is parameterized by a path length $\lambda \epsilon \Lambda = [0, 2\pi R)$, a detector v-axis is parallel to the rotational axis, a $\mu$-axis is parallel to a trajectory tangent vector, I is an iso-center of the imaging apparatus, the detector center is offset from the center of rotation in a transaxial plane by a distance d, and $\overline{SE}$ is a length from the source to a detector element.

22. An apparatus for acquiring projection data at a plurality of angular positions relative to an object disposed in an examination region, the apparatus comprising:

a radiation source;

a radiation sensitive detector which detects radiation emitted by the source that has traversed the examination region, wherein the detector is offset from a center of rotation; and a reconstructor;

wherein the apparatus is adapted to perform a scanning procedure of the object to obtain projection data;

wherein at least one first projection from the projection data is matched with at least one second projection from the projection data, wherein the at least one second projection is measured at an approximately opposing side of an acquisition trajectory from the at least one first projection;

wherein projection data from the at least one second projection is used to derive estimated projection data that is spliced with projection data of the first projection to generate a full, non-truncated projection data set;

wherein the full, non-truncated projection data set is then differentiated with respect to the acquisition trajectory to generate differentiated projection data;

wherein the differentiated projection data is then filtered to generate differentiated and filtered projection data;

wherein redundancy weighting is applied to the differentiated and filtered projection data to generate differentiated, filtered and weighted projection data;

wherein the differentiated, filtered and weighted projection data is then back-projected by the reconstructor to generate volumetric data indicative of the object; and wherein the redundancy weighting comprises applying a redundancy weight $\omega(\mu)$ according to:

$$\omega(u) = \begin{cases} 0, & u_{min} \leq u < u_{-0} \\ \sin^2\left(\frac{\pi}{2}\frac{u-u_{-0}}{\Delta u}\right), & u_{-0} \leq u \leq u_{+0}; \\ 1, & u_{+0} < u \leq u_{max} \end{cases} \text{ and}$$

wherein a $\mu$-axis is parallel to a trajectory tangent vector.

23. An apparatus for acquiring projection data at a plurality of angular positions relative to an object disposed in an examination region, the apparatus comprising:

a radiation source;

a radiation sensitive detector which detects radiation emitted by the source that has traversed the examination region, wherein the detector is offset from a center of rotation; and a reconstructor;

wherein the apparatus is adapted to perform a scanning procedure of the object to obtain projection data;

wherein at least one first projection from the projection data is matched with at least one second projection from the projection data, wherein the at least one second projection is measured at an approximately opposing side of an acquisition trajectory from the at least one first projection;

wherein projection data from the at least one second projection is used to derive estimated projection data that is spliced with projection data of the first projection to generate a full, non-truncated projection data set;

wherein the full, non-truncated projection data set is then differentiated with respect to the acquisition trajectory to generate differentiated projection data;

wherein the differentiated projection data is then filtered to generate differentiated and filtered projection data;

wherein redundancy weighting is applied to the differentiated and filtered projection data to generate differentiated, filtered and weighted projection data;

wherein the differentiated, filtered and weighted projection data is then back-projected by the reconstructor to generate volumetric data indicative of the object; and wherein the reconstructor applies a reconstruction algorithm according to:

$$f_{new}(x) = \frac{1}{2\pi} \int_\Lambda \frac{\omega(u)}{R-(x-I)\cdot\hat{a}} \int_{-\infty}^{\infty} \frac{D}{\overline{SE}(x)} X_d(u', v, \lambda) h_H(u-u') du' (1/R) d\lambda,$$

with $$h_H(\rho) = -\int_{-\infty}^{\infty} i\,\text{sgn}(P) e^{j2\pi\rho P} dP, \text{ and}$$

$$X_d(u, v, \lambda) = \left(\frac{\partial \chi_2}{\partial \lambda} + \frac{\partial \chi_2}{\partial u}\frac{\partial u}{\partial \lambda} + \frac{\partial \chi_2}{\partial v}\frac{\partial v}{\partial \lambda}\right)(u, v, \lambda); \text{ and}$$

wherein D is a distance from the source to the detector, R is a distance from the source to a rotation axis, a circular orbit is parameterized by a path length $\lambda \in \Lambda = [0, 2\pi R)$, a detector v-axis is parallel to the rotational axis, a μ-axis is parallel to a trajectory tangent vector, I is an iso-center of the imaging apparatus, the detector center is offset from the center of rotation in a transaxial plane by a distance d, and $\overline{SE}$ is a length from the source to a detector element.

* * * * *